(12) United States Patent
Cobb

(10) Patent No.: US 6,592,551 B1
(45) Date of Patent: Jul. 15, 2003

(54) SYRINGE PUMPS

(75) Inventor: Anthony Richard Cobb, Brighton (GB)

(73) Assignee: Smith Group PLC, London (GB)

( * ) Notice: Subject to any disclaimer, the term of this patent is extended or adjusted under 35 U.S.C. 154(b) by 0 days.

(21) Appl. No.: 09/562,033

(22) Filed: May 1, 2000

(30) Foreign Application Priority Data

May 12, 1999 (GB) ............................................. 9910985

(51) Int. Cl.$^7$ ............................................. A61M 37/00
(52) U.S. Cl. ................................. 604/155; 128/DIG. 1; 128/DIG. 12
(58) Field of Search .................... 604/67, 151, 152, 604/155, 118, 131, 154, 156; 128/DIG. 1, DIG. 12

(56) References Cited

U.S. PATENT DOCUMENTS

| 4,424,720 A | | 1/1984 | Bucchianeri | |
|---|---|---|---|---|
| 5,545,140 A | * | 8/1996 | Conero et al. | 604/154 |
| 5,814,015 A | * | 9/1998 | Gargano et al. | 664/67 |

FOREIGN PATENT DOCUMENTS

| DE | 298 12 065 | 12/1999 |
|---|---|---|
| EP | 0 567 944 A1 | 11/1993 |
| EP | 0 589 328 A2 | 3/1994 |

* cited by examiner

Primary Examiner—Manuel Mendez
Assistant Examiner—Mark K. Han
(74) Attorney, Agent, or Firm—Connolly Bove Lodge & Hutz LLP; Larry J. Hume

(57) ABSTRACT

A syringe pump has a drive mechanism for moving the plunger of a syringe along a barrel. Ears at the rear of the barrel engage against a wall on the pump and an L shape clamp arm is urged against the ears by a spring. The clamp arm is mounted about an axis at right-angles to the syringe and is articulated at a point along its length. A lever having a flag at one end is pivoted about a horizontal axis by movement of the arm and moves relative to an optical sensor so that the output of the sensor indicates whether the syringe is correctly loaded in the pump. The clamp arm is rotated away from the barrel by the drive mechanism during loading of the syringe.

10 Claims, 2 Drawing Sheets

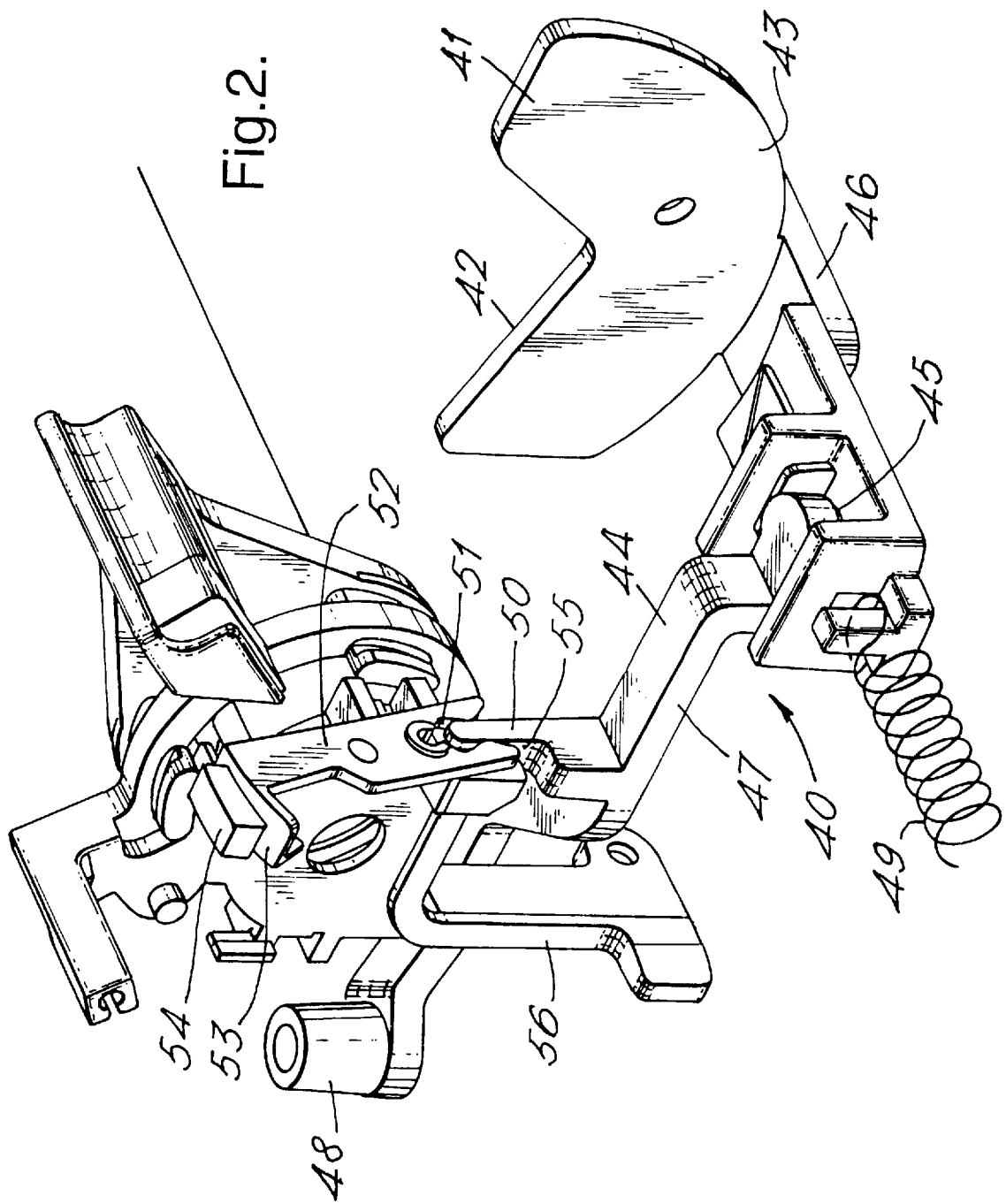

SYRINGE PUMPS

BACKGROUND OF THE INVENTION

This invention relates to syringe pumps.

Syringe pumps are used to supply medication to a patient. A syringe is pre-filled with the medication and this is connected to an infusion line extending to the patient. The syringe is then loaded in the syringe pump, which applies a force to the plunger of the syringe to drive medication into the infusion line at a controlled rate. If the syringe is not correctly loaded in the pump, this could lead to jamming of the pump mechanism and to delays in administering fluid to the patient.

BRIEF SUMMARY OF THE INVENTION

It is an object of the present invention to provide an alternative syringe pump.

According to the present invention there is provided a syringe pump adapted to receive a syringe of the kind having a plunger movable along a barrel with a nose outlet at its forward end and a rear end, the pump including a movable member movable in a first direction towards engagement with a portion at the rear end of the barrel, and means for sensing the position of the movable member to detect whether or not the syringe is correctly positioned in the pump.

The portion at the rear end of the barrel are preferably radially-projecting ears, one side of which may engage a wall on the pump, the movable member engaging the opposite side of the ears. The movable member preferably includes an arm pivoted at one end and having an articulated joint at a location along its length. The means for sensing may include a lever arranged to be pivoted by movement of the arm. The movable member preferably has a pad with a forward face and a V shape edge surface, the forward face engaging the portion at the rear end of the barrel and the V shape edge surface lying against the plunger. The pump may include means moving the movable member in a direction opposite the first direction prior to loading the syringe. The means moving the movable member in the opposite direction may be coupled to a syringe drive mechanism of the pump. The pump may include resilient means arranged to move the movable member in the first direction. The means for sensing preferably includes optical means.

A syringe pump according to the present invention, will now be described, by way of example, with reference to the accompanying drawings.

BRIEF DESCRIPTION OF THE DRAWINGS

FIG. 2 is a perspective view of a part of the pump.

DETAILED DESCRIPTION OF THE PREFERRED EMBODIMENT

Figure 1:
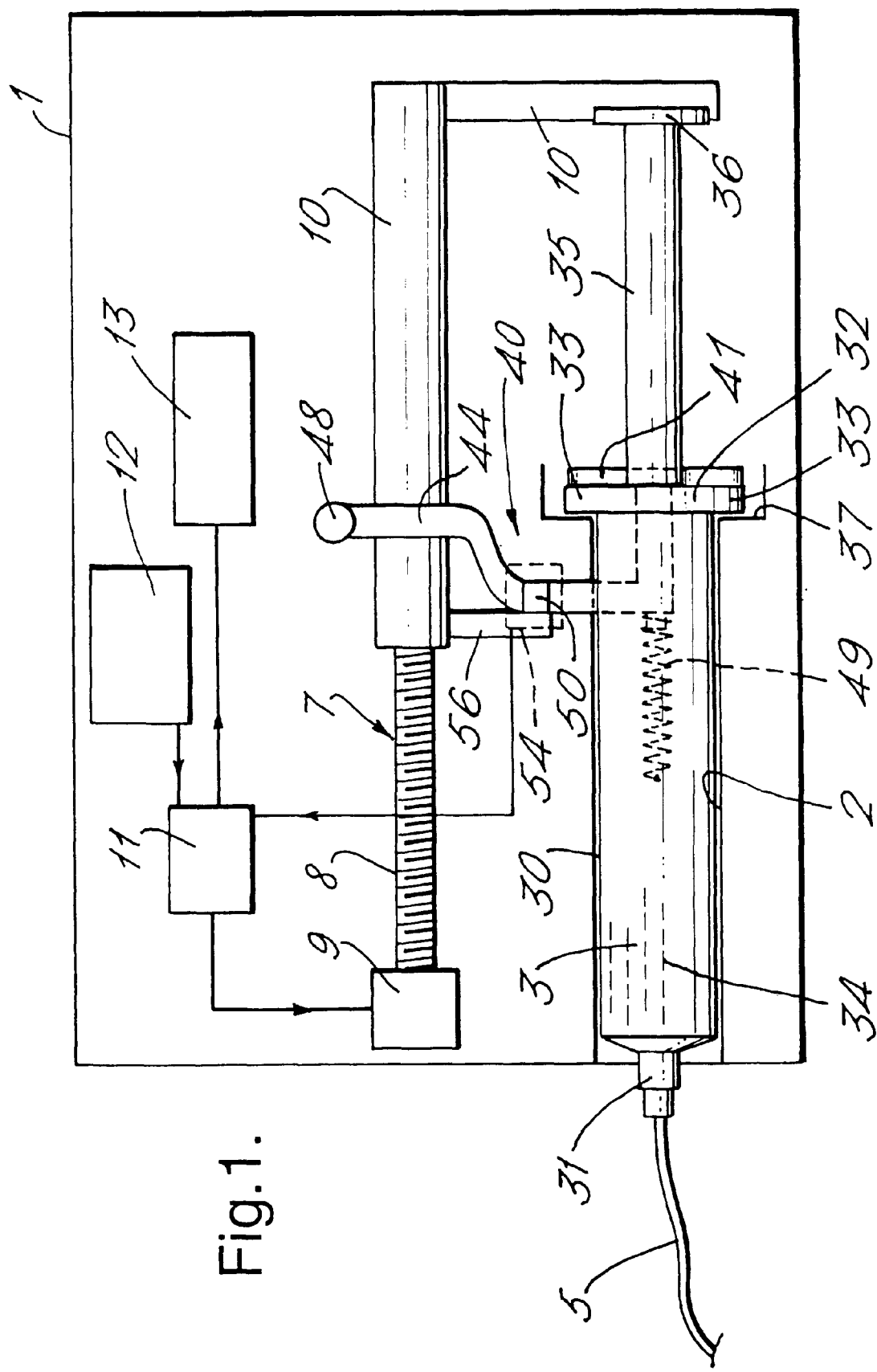
FIG. 1 is a simplified view of the front of the pump.

With reference first to FIG. 1, the pump includes an outer housing 1 with a recess 2 on its front surface shaped to receive a syringe 3 of conventional kind. The syringe 3 has a cylindrical barrel 30 with an outlet or nose 31 at its forward end and an annular projection 32 at its rear end shaped to provide two radially-projecting ears 33 on opposite sides. The syringe 3 contains a medication liquid 34, which is dispensed to a patient via an infusion line 5 connected to the nose 31, by pushing in the plunger 35 of the syringe. The pump has a conventional drive mechanism 7, such as including a lead screw 8 driven by a motor 9, coupled with a mechanism 10 for engaging the head 36 of the plunger 35. The motor 9 is driven by a control unit 11, which receives inputs from a keypad 12, or other user input means, and various sensors. The control unit 11 also provides an output to a display 13.

The forward side of the ears 33 on the syringe barrel 30 abut against a fixed vertical wall 37 in the recess 2, whereas the rear side is contacted by a movable clamp mechanism 40, which is shown more clearly in FIG. 2. The clamp mechanism 40 includes a vertical crescent-shape pad 41 with a V-shape upper surface 42 located to lie against the underside of the plunger 35, with its forward face 43 contacting the rear face of the ears 33. The pad 41 is mounted at one end of an L-shape clamp arm 44 having an articulated joint 45 at its bend enabling limited angular movement between the forward part 46 of the arm, on which the pad is mounted, and the rear part 47 of the arm. The rear part 47 of the arm extends substantially transversely of the axis of the syringe 3 and has a pivotal joint 48 at its end rotatable about a vertical axis at right angles to the axis of the syringe. A spring 49 bears against the arm 44 urging it in a clockwise sense, as viewed from above, so that the pad 41 is pulled forwardly by the spring to clamp the ears 33 against the wall 37.

About midway along its length, the rear part 47 of the arm 44 has a vertically-projecting pawl finger 50, which engages a slot 51 in the lower end of a lever 52. The lever 52 is pivoted about a horizontal axis midway along its length and its upper end is formed with a curved flag 53. The flag 53 is located adjacent an opto-electronic sensor 54 and is moved relative to the sensor in response to movement of the arm 44. The pawl finger 50 also has a vertical, forwardly-facing contact surface 55. The contact surface 55 is located for engagement by a cooperating contact surface on an actuating arm 56 coupled with the plunger engaging mechanism 10. This is arranged so that, when the plunger engaging mechanism 10 is at its rearmost position, such as for loading or unloading of the syringe 3, the actuating arm 56 engages the pawl finger 50 on the arm 44 and displaces the pad 41 rearwardly.

In operation, therefore, when the pump is set for loading the syringe 3, the ear clamp mechanism 40 is open to enable the syringe to be loaded freely into the recess 2. As soon as the plunger engaging mechanism 10 is displaced forwardly to engage the plunger head 36, the actuating arm 56 disengages the arm 44, allowing its spring 49 to bring the pad 41 into contact with the rear of the ears 33 on the syringe barrel 30. This clamps the ears 33 and hence the syringe 3 in position. If the syringe 3 is correctly loaded, the arm 44, and the flag 53, will lie at a defined position and the sensor 54 will, therefore, provide an output to the control unit 11 indicative of correct syringe loading. The pump then proceeds with its normal operation. If, however, the syringe 3 were incorrectly loaded in such a way that its ears 33 were not correctly positioned against the wall 37, the arm 44 would either move beyond its correct rest position or would be prevented from moving as far as this. In either case, the control unit 11 would identify an incorrect output from the sensor 54 and prevent further operation of the pump. The control unit 11 would also generate an output to the display 13 to notify the user of incorrect syringe loading.

The syringe pump of the present invention provides a rapid warning of incorrect syringe loading, thereby reducing the risk of problems that this might cause.

What I claim is:

1. A syringe pump comprising:
   a syringe drive mechanism; a location to receive a syringe of the kind having a plunger movable along a barrel,
   said barrel having an outlet at its forward end and a rear end,
   said rear end having a portion projecting radially outwardly;
   a movable member movable in a first direction towards engagement with said portion at said rear end of said barrel; and
   a sensor for sensing the position of said movable member to detect whether or not said rear end of the barrel is correctly positioned,
   wherein said syringe drive mechanism is coupled with said movable member such that said movable member is moved in a direction opposite said first direction prior to loading said syringe.

2. A syringe pump according to claim 1, wherein said portion at said rear end of said barrel includes radially-projecting ears.

3. A syringe pump according to claim 1 including resilient means arranged to move said movable member in said first direction.

4. A syringe pump according to claim 1, wherein the said sensor is an optical sensor.

5. A syringe pump comprising:
   a syringe drive mechanism; a location to receive a syringe of the kind having a plunger movable along a barrel,
   said barrel having an outlet at its forward end and a rear end,
   said rear end having a portion projecting radially outwardly;
   a movable member movable in a first direction towards engagement with said portion at said rear end of said barrel; and
   a sensor for sensing the position of said movable member to detect whether or not said rear end of the barrel is correctly positioned,
   wherein said portion at said rear end of said barrel includes radially-projecting ears,
   wherein one side of said ears engage a wall on the pump, and wherein said movable member engages an opposite side of said ears.

6. A syringe pump comprising:
   a syringe drive mechanism; a location to receive a syringe of the kind having a plunger movable along a barrel,
   said barrel having an outlet at its forward end and a rear end,
   said rear end having a portion projecting radially outwardly;
   a movable member movable in a fist direction towards engagement with said portion at said rear end of said barrel; and
   a sensor for sensing the position of said movable member to detect whether or not said rear end of the barrel is correctly positioned,
   wherein the said movable member includes an arm, a pivot at one end of said arm and an articulated joint at a location along the length of said arm.

7. A syringe pump according to claim 6, wherein said sensor includes a lever engaged with said arm so that the lever is displaced by movement of said arm.

8. A syringe pump comprising:
   a syringe drive mechanism; a location to receive a syringe of the kind having a plunger movable along a barrel,
   said barrel having an outlet at its forward end and a rear end,
   said rear end having a portion projecting radially outwardly;
   a movable member movable in a first direction towards engagement with said portion at said rear end of said barrel; and
   a sensor for sensing the position of said movable member to detect whether or not said rear end of the barrel is correctly positioned,
   wherein said movable member has a pad with a forward face and a V shape edge surface, and
   wherein said forward face engages the said portion at the said rear end of said barrel and, said V shape edge surface lies against said plunger.

9. A syringe pump comprising:
   a syringe drive mechanism;
   a location to receive a syringe of the kind having a plunger movable along a barrel,
   said barrel having an outlet at its forward end and a rear end,
   said rear end having a portion that projects radially outwardly;
   a clamp arm movable in a first direction towards engagement with said portion at the said rear end of said barrel;
   an actuating arm displaceable with the syringe drive mechanism so as to move said clamp arm away from said barrel during loading of a syringe; and
   a sensor for sensing the position of said clamp arm to detect whether or not said rear end of said barrel is correctly positioned.

10. A syringe pump comprising:
    a syringe drive mechanism;
    a location to receive a syringe of the kind having a plunger movable along a barrel,
    said barrel having an outlet at its forward end and a rear end;
    an L shape clamp arm pivoted at one end about an axis at right angles to the axis of the syringe,
    said clamp arm having an articulated joint at a point along its length and having a pad at its opposite end adapted to move forwardly of the syringe to contact the rear end of the barrel;
    an optical sensor; and
    a sensor lever coupled at one end with said clamp arm and pivoted about an axis at right angles to the axis about which the clamp arm is pivoted,
    the opposite end of said sensor lever having a flag movable relative to said optical sensor such that said sensor provides an output indicative of the position of said clamp arm.

* * * * *